United States Patent [19]

Sebag et al.

[11] Patent Number: 4,940,573
[45] Date of Patent: Jul. 10, 1990

[54] CATIONIC SURFACE-ACTIVE COMPOUNDS

[75] Inventors: Henri Sebag, Paris; Guy Vanlerberghe, Claye-Souilly, both of France

[73] Assignee: L'Oreal, Paris, France

[21] Appl. No.: 282,321

[22] Filed: Dec. 9, 1988

Related U.S. Application Data

[60] Division of Ser. No. 102,818, Sep. 23, 1987, Pat. No. 4,820,820, which is a continuation of Ser. No. 276,817, Jun. 24, 1981, abandoned.

[30] Foreign Application Priority Data

Jun. 25, 1980 [FR] France ................................ 80 14148

[51] Int. Cl.[5] ............................................. A61L 9/04
[52] U.S. Cl. ........................................ 424/45; 424/70; 424/71; 544/174; 544/177
[58] Field of Search ............................ 424/45, 70, 71; 544/174, 177

[56] References Cited

U.S. PATENT DOCUMENTS

| | | | |
|---|---|---|---|
| 3,879,464 | 4/1975 | Kalopissis et al. | 260/584 C |
| 4,009,255 | 2/1977 | Kalopissis et al. | 424/71 |
| 4,096,332 | 6/1978 | Kalopissis et al. | 544/177 |
| 4,138,427 | 2/1979 | Vanlerberghe et al. | 260/459 A |
| 4,189,468 | 2/1988 | Vanlerberghe et al. | 424/71 |
| 4,199,562 | 4/1980 | Vanlerberghe et al. | 424/47 |

FOREIGN PATENT DOCUMENTS

2027725 2/1980 United Kingdom .

Primary Examiner—Ellis P. Robinson
Assistant Examiner—P. L. Prater
Attorney, Agent, or Firm—Fleit, Jacobson, Cohn, Price, Holman & Stern

[57] ABSTRACT

Cationic surface-active products of the formula:

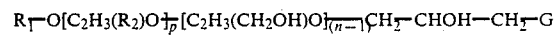

in which $R_1 = C_4-C_{20}$ aliphatic radical, $R_2 = C_4-C_{20}$ alkyl, alkoxymethyl or alkenyloxy radical, $p = 1-2.5$, $n = 2-20$ and G denotes an amine or amine oxide group, and their salts are disclosed for use principally in cosmetics.

8 Claims, No Drawings

CATIONIC SURFACE-ACTIVE COMPOUNDS

This is a divisional of application Ser. No. 102,818 filed Sept. 23, 1987 now U.S. Pat. No. 4,820,820, which is a continuation application of Ser. No. 276,817, filed Jun. 24, 1981, now abandoned.

The present invention relates to cationic surface-active compounds, a process for their preparation, the compositions in which they are present and their use, in particular in cosmetics and especially for treating the hair or skin.

Cationic surface-active agents have been known for a long time for treating the hair. They make it possible, in particular. to give the hair a softer feel, to make it easier to comb out and to impart shine. However, the use of these surface-active agents involves certain disadvantages, the most substantial of which are weighing-down of the hair and its greasy appearance. Furthermore, numerous surface-active agents exhibit a certain aggressiveness, which can cause irritation to the skin or the mucous membranes of the eye.

The products of the present invention make it possible to reduce or eliminate these disadvantages without loss in quality of the cosmetic properties. In fact, they make it possible to impart softness and shine to the hair without resulting in weighing-down or a greasy appearance. Furthermore, the biological properties are good and the products are very much better tolerated by the mucous membranes of the eye and by the skin. Moreover, they permit the preparation of stable cationic emulsions and more particularly of oil-in-water emulsions. The compounds according to the invention comprise a lipophilic part, consisting of at least two fatty chains, which is joined to a polyhydroxylic polyether hydrophilic part having a cationic end group. It might have been expected that the presence of two fatty chains or more than two fatty chains in the lipophilic part would have a weighing-down effect on the hair. Surprisingly, it is found that the cationic surface-active agents according to the invention weigh the hair down less than the corresponding cationic surface-active agents containing only one fatty chain in the lipophilic part.

Thus the products of this invention provide better cosmetic properties and notably weigh-down the hair less than the products described in French Patent No. 1,538,525, British Specification No. 1,178,873 and U.S. Pat. Nos. 3,879,464 and 4,009,255.

The products of this invention further provide the advantage over those described in the above patents and in British Specification No. 2,027,725 and U.S. Ser. No. 56,110 of Jul. 9, 1979 of enabling one to prepare stable cationic emulsions. Again the products of this invention provide, in spite of the presence of two lipophilic chains, very good solubility in water, in particular at neutral or acid pH.

The products of the invention also possess the advantage that, if desired, they can be prepared by a simplified process. In fact, it is possible to omit the step for purification of the mixture of intermediates obtained by reacting the alcohol with the compound having an epoxide end group. According to the invention, it is possible to condense a mixture of oligomers, and this reduces manufacturing costs.

The compounds of the invention are soluble or dispersible in water or in an aqueous-alcoholic medium.

The products of the invention can be represented by the general formula (I)

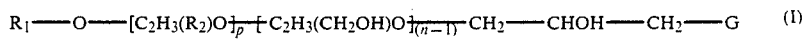

$$R_1\text{---}O\text{---}[C_2H_3(R_2)O]_p\text{---}[C_2H_3(CH_2OH)O]_{(n-1)}\text{---}CH_2\text{---}CHOH\text{---}CH_2\text{---}G \quad (I)$$

in which:
$R_1$ denotes a linear or branched, saturated or unsaturated aliphatic radical containing from 4 to 20 carbon atoms, advantageously from 6 to 18 carbon atoms and more advantageously from 4 to 18 carbon atoms;

$R_2$ is chosen from the group comprising:
(1) a preferably linear alkyl radical,
(2) a linear or branched alkoxymethyl radical, and
(3) a preferably linear alkenyloxy radical, the alkyl or alkenyl parts of these radicals containing from 4 to 20 carbon atoms, advantageously from 8 to 20 carbon atoms and preferably from 8 to 18 carbon atoms;

p is equal to 1 or alternatively denotes an integer or decimal number from 1 to 2.5 and represents an average statistical value (in a mixture of compounds);

n denotes an integer or decimal number from 2 to 20 and preferably from 2 to 15 and represents an average statistical value; and G is chosen from the group comprising:

(a)

(b)

(c)

in which x denotes zero or 1, and

(d)

in which $R_3$ and $R_4$ denote a lower alkyl or lower hydroxyalkyl radical having from 1 to 3 carbon atoms, and preferably a methyl, ethyl, isopropyl or hydroxyethyl radical, or alternatively $R_3$ and $R_4$ are joined directly, or via a hetero-atom, to the nitrogen atom to form a 5- or 6-membered heterocyclic ring and preferably a pyrrolidine, piperidine, morpholine or N-methyl-piperazine heterocyclic ring;

$V^-$ denotes an anionic radical of a mineral or organic acid, and preferably a chloride, bromide, sulphate, phosphate, acetate, lactate, tartrate, citrate or gluconate anion;

$R_5$ denotes an alkyl or hydroxyalkyl radical having 1 to 3 carbon atoms, and preferably a methyl, ethyl, hydroxyethyl or dihydroxypropyl radical;

$Y^-$ denotes an anion and preferably a methylsulphate, methanesulphonate, p-toluenesulphonate, chloride, bromide or iodide anion; and $T^-$ denotes a methylcarboxylate or propylsulphonate anion.

In the preferred embodiments of the invention:

$R_1$ preferably denotes a straight-chain or branched-chain alkyl or alkenyl radical, especially a radical chosen from butyl, hexyl, octyl, decyl, dodecyl, tetradecyl, hexadecyl, octadecyl, oleyl, 2-ethylhexyl, 2-butyloctyl and 2-hexyldecyl groups, or a mixture of these radicals (in a mixture of compounds); and $R_2$ preferably denotes a radical chosen from butyl, hexyl, octyl, decyl, dodecyl, tetradecyl, hexadecyl and octadecyl groups, the alkoxymethyl radicals derived from the above groups, or also 2-ethylhexyloxymethyl, 2-butyloctyloxymethyl, 2-hexyldecyloxymethyl, 2-octyldodecyloxymethyl and oleyloxymethyl radicals, or a mixture of these radicals (in a mixture of compounds).

In the formula (I), the group $[C_2H_3(R_2)-O]$ denotes the two isomers:

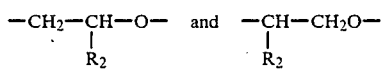

and the group $[C_2H_3(CH_2OH)O]$ denotes the two isomers:

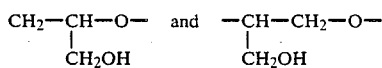

The invention also relates to a process for the preparation of the compounds or mixture of compounds of the formula (I).

The compounds of the formula (I) can be prepared in accordance with a multi-stage process. A mixture of compounds is generally obtained.

A. Firstly, the compounds of the formula (II):

$$R_1-O[C_2H_3(R_2)-O]_pH \qquad (II)$$

in which $R_1$ and $R_2$ and p have the same meanings as those indicated above, are prepared by reacting an alcohol of the formula $R_1OH$ with a compound having an epoxide end group, of the formula:

in which the group $R_2$ has the same meaning as that indicated above.

This reaction is suitably carried out in the presence of a Lewis acid catalyst, such as boron trifluoride, stannic chloride or antimony pentachloride, in an amount of 0.2 to 5% by weight, relative to the reaction mixture, and at a temperature of 20° to 120° C. and preferably 50° to 100° C.

It can also be carried out in the presence of an alkaline catalyst such as sodium or potassium or the methylate, ethylate or tert.-butylate of sodium or potassium in an amount of 0.2 to 15%, and preferably 0.5 to 10%, relative to the reaction mixture, at a temperature of 100° to 180° C. and preferably 100° to 150° C.

The reaction can be carried out with the stoichiometric proportions of alcohol $R_1OH$ and of epoxide compound, but preferably in the presence of an excess of one or other of the reactants. When the alcohol is used in excess, the unreacted alcohol can be removed by distillation. In the opposite case, when the epoxide is in excess, it reacts completely to give compounds of the formula (II) containing more than two lipophilic chains.

The molar proportions of alcohol $R_1OH$, relative to the epoxide (III), are suitable from 0.4/1 to 10/1.

It is possible, if appropriate, to use an aliphatic or aromatic hydrocarbon as solvent, although this is not generally necessary.

The reactants which have not reacted can be removed under reduced pressure.

The compounds of the formula (II) thus obtained can be used either as such or after purification by distillation under reduced pressure.

By omitting the distillation, the process of preparation is simplified and a mixture of compounds of the formula (II), in which p denotes an average statistical value, is usually obtained.

After one molecule of epoxide has reacted per molecule of alcohol $R_1OH$, two possible compounds having the structures represented by the formulae:

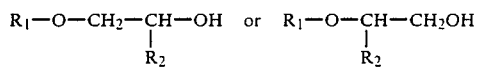

are obtained, depending on the direction of opening of the oxirane ring.

B. In a second stage, a mixture of intermediates of the general formula (IV):

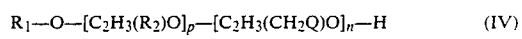

in which $R_1$, $R_2$, p and n have the same meaning as above and in which Q denotes a chlorine or bromine atom, is prepared by telomerising epichlorohydrin or epibromohydrin with the product of formula (II) as telogen.

More particularly, the compounds of the formula (IV) can be prepared by reacting a compound of the formula (II) containing two lipophilic chains, or a mixture of compounds of the formula (II) containing two or more lipophilic chains, with n molecules of epichlorohydrin or epibromohydrin, in the presence of an acid catalyst and, if appropriate, a solvent.

Depending on whether a compound or a mixture of compounds of the formula (II) is reacted, p, in the formula of the intermediates of the formula (IV), denotes the number 1 or an average statistical value of 1 to 2.5.

The acid catalyst can be a Lewis acid such as boron trifluoride, stannic chloride or antimony pentachloride in an amount of 0.2 to 5% by weight, relative to the reaction mixture, and the reaction is suitably carried out at a temperature of 20° to 120° C. and preferably 50° to 100° C.

If they are used, the solvents are particularly aromatic hydrocarbons such as benzene, toluene or xylene, or aliphatic hydrocarbons such as hexane or heptane.

Preferably, the compounds of the formula (IV) are prepared in the absence of a solvent.

The n molecules of epihalogenohydrin give rise to the formation of a mixture of compounds containing a number of halogen-containing units which is less than, equal to or greater than the value of n, the latter representing a number-average statistical value.

During this reaction, depending on the direction of opening of the epoxide group, it is possible to obtain two structures for the halogen-containing unit, these structures being represented by the summary formula:

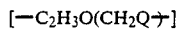

and by the structural formulae:

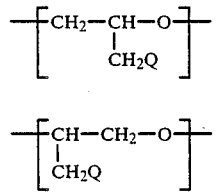

Although the configuration (V) is the more probable, a certain proportion of units of the structure (VI) can be present.

C. In a third stage, the products of the formula VII

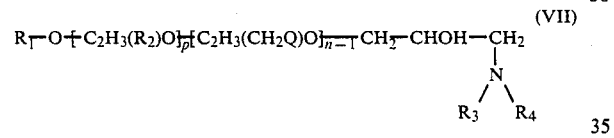

are obtained by reacting the products (IV) with a secondary amine:

In formulae (VII) and (VIII), $R_1$, $R_2$, $R_3$, $R_4$, Q, n and p have the same meanings as above.

The compounds (VIII) are used in stoichiometric proportions or in excess, relative to the compounds (IV), these proportions generally varying from 1/1 to 2.5/1.

The reaction can be carried out without a solvent, or preferably in the presence of a solvent, which is generally an alcohol, a glycol, a polyglycol or an alkyl ether of a glycol or polyglycol, for example methanol, ethanol, propanol, isopropanol, t-butanol, ethylene glycol, propylene glycol, butylene glycol, diethylene glycol or dipropylene glycol, the methyl, ethyl or butyl ether of ethylene glycol, the butyl ether of diethylene glycol or the isobutyl ether of dipropylene glycol.

The reaction temperature is generally 50° C. to 110° C. and the reaction can be carried out, if appropriate, in the presence of an alkali such as sodium hydroxide or potassium hydroxide. The use of the alkali becomes necessary when the proportions of the compounds (VIII) and (VI) are close to the stoichiometric proportions.

The excess of compounds (VIII), the salts and the solvents can be removed by washing with water at, say, 80°-90° C. and then by distillation under reduced pressure.

D. The products of the invention are obtained from the products (VII), which are first heated in the presence of sodium acetate or potassium acetate, in a solvent of the glycol or glycol ether type, such as ethylene glycol, propylene glycol, butylene glycol, diethylene glycol; dipropylene glycol, the butyl ether of diethylene glycol or the isobutyl ether of dipropylene glycol, typically at a temperature of 180° C. to 190° C., for 3 to 6 hours.

After the inorganic salts have been filtered off and the solvents have been removed under reduced pressure, the acetic acid esters formed can be saponified in the presence of concentrated sodium hydroxide or potassium hydroxide solution and washed with water, or alcoholised in absolute methanol or ethanol, in the presence of sodium methylate or ethylate or potassium methylate or ethylate.

After removal of the solvents under reduced pressure and, if appropriate, oxidation and/or salification with a mineral or organic acid, on the one hand, and/or quaternisation or betainisation, on the other hand, the product of the invention of the formula (I), in which G respectively has the meanings (a), (b), (c) or (d) below

are obtained.

The oxidation, salification, quaternisation or betainisation reactions are suitably carried out, with or without a solvent, at a temperature of 10° to 80° C.

"Botainisation", as used herein, is to be understood as meaning quaternisation carried out with sodium chloroacetate or methyl or ethyl chloroacetate or with propane-sultone.

The customary solvents, such as alcohols, glycols, short-chain alkyl ethers of glycols, acetone and/or water, can be used for these reactions. For the alkylation reactions, chlorinated solvents and aliphatic or aromatic hydrocarbons can also be used.

The following may be mentioned amongst the preferred alkylating agents: methyl or ethyl sulphate, methanesulphonate or para-toluenesulphonate, methyl or ethyl chloride, bromide or iodide, methyl or ethyl chloroacetate, sodium chloroacetate, propane-sultone, glycol chlorohydrin, glycol bromohydrin and glycerol chlorohydrin or bromohydrin.

The oxidation reactions are generally carried out in the presence of hydrogen peroxide.

The products of the invention of the formula (I) are generally in the form of an oil, paste or wax. They are soluble or dispersible in water.

This invention also provides compositions containing at least one cationic surface-active agent of the formula (I) together with a carrier or diluent, in particular compositions for use in cosmetic or pharmaceutical applications, and more particularly cosmetic compositions for treating the hair or skin. These compositions are generally presented in the form of an aqueous or aqueous-alcoholic solution or dispersion, in the form of a gel or a water-in-oil or oil-in-water emulsion or microemulsion, in the form of an oily or oily-alcoholic composition, or in the form of a wax, or are packaged in an aerosol, and they generally contain a product of the formula (I) in an amount of 0.05 to 100% and preferably of 0.2 to 20% by weight, relative to the total weight of the composition.

"Microemulsion" is to be understood as meaning a very fine emulsion which cannot be resolved in an optical microscope. "Aqueous-alcoholic solutions" are to be understood as meaning solutions containing water and an alcohol having 2 to 6 carbon atoms, and/or one or more glycols and/or glycol ethers. The aqueous-alcoholic solutions generally contain from 20 to 70% by weight of alcohol preferably ethanol or isopropanol.

The oil-in-water emulsions preferably contain 25 to 85% by weight of water, 2 to 20% by weight of product of formula (I) and 5 to 60% by weight of animal, vegetable or mineral oil, or an oil of synthetic origin, based on the weight of the emulsion.

"Oily composition" or "bath oil" is to be understood as meaning a composition in which the vehicle consists of an oil or a mixture of oils of animal, vegetable, mineral or synthetic origin. An oily composition can also consist solely of a mixture of products of the formula (I), without other adjuvants.

"Oily-alcoholic composition" is to be understood as meaning a composition in which the vehicle consists of 10–90% by weight of one or more alcohols and one or more oils or waxes of animal, vegetable, mineral or synthetic origin.

The compositions can also be presented in the form of a powder, a cream or a milk or be packaged in aerosols.

The pH of the compositions is generally from 3 to 11 and preferably from 3.5 to 8.5.

The products according to the invention can be used as treating agents for the head of hair or the skin, as a wetting agent, emulsifying agent, dispersing agent, solubilising agent or superfatting agent, as an emollient or as an excipient.

Examples of cosmetic compositions which may be mentioned are shampoos, rinsed lotions (rinses), wave-setting lotions, products for shaping the head of hair (brushing lotions), perming compositions, dyeing compositions, anti-acne compositions, beauty milks and creams and compositions for the bath.

The cosmetic compositions containing one or more products according to the invention can also contain other constituents such as non-ionic, anionic, cationic or amphoteric surface-active agents, animal, mineral, vegetable or synthetic oils or waxes, anionic, cationic, non-ionic or amphoteric resins or polymers normally used in cosmetics, thickeners, opacifiers, preservatives, perfumes, dyestuffs, alcohols, glycols or glycol ethers having 2 to 6 carbon atoms, pH modifiers, inorganic salts, natural substances, and substances which are active in the treatment, care or protection of the skin or hair.

The present invention also provides a process for treating the hair or skin, which consists in applying, to the hair or skin, a sufficient amount of a composition of this invention.

The following Examples further illustrate the present invention.

PREPARATION EXAMPLES

EXAMPLE 1

Preparation of a mixture of compounds of the formula (I) in which:
$R_1$ denotes the radical $C_8H_{17}$
$R_2$ denotes the radical $C_{16}H_{33}$
$p = 1$
$n = 2$
$G =$

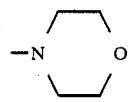

(a) Preparation of the intermediate of the general formula (II) in which $R_1$, $R_2$ and p have the same meaning as above 8.5 g (50 meq) of sodium methylate dissolved in methanol are added to 390 g (3 mols) of n-octanol. The methanol is removed by heating under reduced pressure, the temperature is then raised to 150° C., under a nitrogen atmosphere, and 268 g (1 mol) of 1,2-epoxyoctadecane are added dropwise. After the addition, the temperature is kept at 150° C. for 3 hours 30 minutes and the product is then washed three times with 800 ml of boiling water.

The organic phase is heated under reduced pressure in order to remove the water and the excess octanol.

The residue is distilled at 193°–205° C./0.133 mbar. The product obtained is a white solid with a melting point of 49° C.

(b) Preparation of the mixture of polychlorinated compounds of the formula (IV)

0.15 ml of $BF_3$ etherate is added to 40 g (0.1 mol) of the product described in paragraph (a), and the temperature is then raised to 60° C.

18.5 g (0.2 mol) of epichlorohydrin are added dropwise. The temperature is kept at 60° C. for 1 hour after the addition has ended.

(c) Preparation of the mixture of compounds of the formula (VII)

8.7 g (0.1 mol) of morpholine are added to 56 g (0.096 mol) of the polychlorinated derivative thus obtained, and 11.5 g of an aqueous solution of NaOH containing 10 meq/g are then added dropwise. The temperature of the mixture is raised to 80° C. for 1 hour 30 minutes. 80 ml of boiling water are then added and the organic phase is separated off, washed again with 60 ml of hot water and dried by heating under reduced pressure.

The base number of the product obtained is 1.31 meq/g and the chlorine number is 1.77 meq/g.

(d) Preparation of the mixture of compounds (I) according to the invention.

9.3 g (95 meq) of anhydrous potassium acetate are added to 54 g of the chlorinated derivatives obtained above (95 meq of organic chlorine), solubilised in 54 g of dipropylene glycol.

The mixture is heated at 180° C. for 5 hours.

The potassium chloride formed is filtered off and the dipropylene glycol is distilled under reduced pressure.

The product thus obtained is dissolved in 60 ml of absolute ethanol in the presence of 0.5 g of a 30% strength solution of sodium methylate in methanol.

The solution is left for 24 hours at ambient temperature, the volatile products are distilled and the residue is then washed three times with 60 ml of boiling water.

The dried product is a brown oil. Amine number: 1.30 meq/g.

EXAMPLE 2

Preparation of a mixture of compounds of the general formula (I) in which:
$R_1 = C_8H_{17}$
$R_2 = C_{16}H_{33}$
$p = 1$
$n = 4$
$G =$

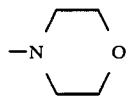

(a) Preparation of the mixture of polychlorinated compounds of the formula (IV)

1.2 ml of boron trifluoride/ether complex are added to 239 g (0.6 mol) of the product obtained in accordance with Example 1 (a), and 222 g (2.4 mols) of epichlorohydrin are then added dropwise at 55° C., whilst stirring.

(b) Preparation of the mixture of compounds of the general formula (VII)

229 g (0.3 mol) of the chlorinated derivative thus obtained are solubilised in 220 g of dipropylene glycol, and 27.5 g (0.31 mol) of morpholine are then added.

31.5 g of an aqueous solution of NaOH containing 10 meq/g (315 meq) are subsequently added dropwise and the mixture is then heated for 1 hour at 85° C.

(c) Preparation of the mixture of compounds (I) of the invention 119 g (1.21 mols) of anhydrous potassium acetate are then added to the reaction medium and the mixture is heated at 180° C., under a stream of nitrogen, for 5 hours 30 minutes.

The potassium chloride formed is filtered off and the filtrate is concentrated by heating under reduced pressure.

The residue is solubilised in 256 g of n-butanol, in the presence of 2.1 g of a 30% strength solution of sodium methylate in methanol. The solution is left for 48 hours at ambient temperature.

This solution is subsequently washed twice with 400 ml of boiling water, and the organic phase is then dried by heating under reduced pressure.

A brown liquid is thus obtained, which is soluble in water after neutralisation with excess lactic acid.

Amine number: 1.26–1.28 meq/g.

EXAMPLE 3

Preparation of a mixture of compounds of the general formula (I) in which:
$R_1 = C_8H_{17}$
$R_2 = C_{16}H_{33}$
$p = 1$
$n = 2$
$G =$

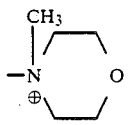

17.8 g (0.141 mol) of dimethyl sulphate are added dropwise at ambient temperature, whilst stirring, to 111 g (that is to say 141 meq of basic groups) of products prepared in accordance with Example 2.

The temperature is left to rise to 40° C. and this temperature is maintained for 2 hours.

The product obtained is in the form of a water-dispersible brown paste.

EXAMPLE 4

Preparation of a mixture of compounds of the general formula (I) in which:
$R_1 = C_{10}H_{21}$
$R_2 = C_{14}H_{29}$
$p = 1$
$n = 2$
$G =$

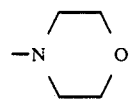

(a) Preparation of the intermediate of the formula (II)

12.8 g (75 meq) of sodium methylate dissolved in methanol are added to 711 g (4.5 mols) of decan-1-ol marketed under the name Alfol 10 by CONDEA.

The methanol is removed by heating under reduced pressure.

The residue is heated to a temperature of 150° C. and 360 g, that is to say 1.5 mols, of 1,2-epoxyhexadecane are added in the course of about 2 hours.

The temperature is maintained for 3 hours 30 minutes after the addition.

The product thus obtained is washed twice with its own weight of boiling water, and the water and the excess alcohol are then evaporated off under reduced pressure.

The product obtained is distilled at 187°–195° C./0.0931 mbar. A white wax having a melting point of 50° C. is obtained.

Hydroxyl number: 2.40–2.32 meq/g.

(b) Preparation of the mixture of polychlorinated compounds of the formula (IV)

0.48 ml of BF$_3$ etherate is added to 132 g (0.33 mol) of the product thus obtained, in the molten state, and 61.4 g (0.66 mol) of epichlorohydrin are then introduced dropwise, whilst keeping the temperature at 60° C.

This temperature is maintained for 30 minutes after the addition has ended.

OH number; 1.77 meq/g.

(c) Preparation of the mixture of compounds of the formula (VII)

31 g (0.35 mol) of morpholine are added to 192 g (0.33 mol) of the product described above and the temperature is kept at 90° C. for 1 hour, whilst stirring. 36 g of a 40% strength aqueous solution of NaOH (0.36 mol) are then added dropwise. The mixture is kept at 90° C. for a further 2 hours, whilst stirring, and then washed three times with its own weight of hot water.

The mixture is then dried by heating under reduced pressure.

A colourless liquid is obtained.

Base number: 1.40 meq/g.

Chlorine number: 1.46 meq/g.

(d) Preparation of the mixture of compounds of the general formula (I)

190 g of dipropylene glycol and 28.6 g (that is to say 290 meq) of anhydrous potassium acetate are added to 190 g (that is to say 278 meq of chlorine) of the product obtained above.

The mixture is heated to 180° C. under a stream of nitrogen.

The mixture is kept at this temperature for 5 hours; the temperature is left to return to 90° C.

An equal weight of water at 90° C. is then added to the mixture, whilst stirring. The aqueous phase is drawn off and 28 g of a 40% strength aqueous solution of NaOH (that is to say 280 meq) are added to the organic phase thus obtained.

The reaction medium is kept at 80° C. for 1 hour and then washed three times with an equal amount of hot water.

The medium is dried by heating under reduced pressure.

A red-brown liquid of high viscosity is obtained, which is soluble in water in the presence of lactic acid.

Amine number: 1.50 meq/g.

OH number: 2.79 meq/g.

EXAMPLE 5

Preparation of a mixture of compounds of the general formula (I) in which:

$R_1 = C_{10}H_{21}$
$R_2 = C_{14}H_{29}$
$p = 1$
$n = 2$
$G =$

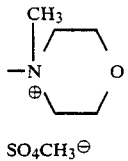

$SO_4CH_3^{\ominus}$ 253 g (that is to say 2,004 meq) of freshly distilled dimethyl sulphate are added dropwise at ambient temperature, whilst stirring, to 1,410 g (that is to say 2,110 meq of basic groups) of compounds prepared in accordance with Example 4, diluted with 141 g of absolute ethanol. The temperature of the mixture is left to rise to 50° C. and this temperature is maintained for 2 hours. The ethanol is then distilled by heating under reduced pressure; a brown product is obtained, which can be diluted with water.

EXAMPLE 6

Preparation of a mixture of compounds of the general formula (I) in which:

$R_1 = C_{10}H_{21}$
$R_2 = C_{14}H_{29}$
$p = 1$
$n = 2$
$G =$

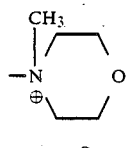

$CH_3SO_3^{\ominus}$ 7.75 g of methyl methanesulphonate are added dropwise to 50 g (0.08 mol) of compounds obtained in accordance with Example 4, heated to 50° C. The temperature is kept at 50° C. for a further 2 hours after the addition has ended.

A water-dispersible paste is thus obtained.

EXAMPLE 7

Preparation of a mixture of compounds of the general formula (I) in which:

$R_1 = C_{10}H_{21}$
$R_2 = C_{14}H_{29}$
$p = 1$
$n = 5$
$G =$

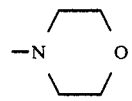

(a) Preparation of the mixture of polychlorinated compounds of the formula (IV)

2.1 ml of $BF_3$ etherate are added to 239 g (0.6 mol) of the derivative obtained in accordance with Example 4 (a), in the molten state, and 277.5 g (3 mols) of epichlorohydrin are then added dropwise, whilst keeping the temperature at 55° C.

The product thus obtained is washed twice with 500 ml of water at 90° C. and then dried by heating under reduced pressure.

The most volatile constituents are then removed by molecular distillation at 220° C./$1.33.10^{-3}$ mbars.

(b) Preparation of a mixture of compounds of the general formula (VII).

27.8 g (0.319 mol) of morpholine are added to 262 g of the chlorinated derivatives thus obtained, 32 g of a 40% strength solution of NaOH are then added, the temperature is raised to 80° C. for 2 hours and the mixture is then washed four times with an equal weight of boiling water. It is subsequently dried by heating under reduced pressure.

An amber-coloured oil is obtained.

Base number: 1 meq/g.

(c) Preparation of the mixture of compounds of the general formula (I)

92.6 g (that is to say 944 meq) of anhydrous potassium acetate are added to 205 g (that is to say 900 meq of Cl) of the product obtained in accordance with Example 4 (b), dissolved in 205 g of butyldiglycol, and the mixture is heated at 180° C. for 6 hours.

The potassium chloride formed is separated off and the solution is concentrated by heating to 180° C. under reduced pressure.

The product thus obtained is solubilised in 250 g of absolute ethanol, and 1.7 g (that is to say 10.5 meq) of a solution of sodium methylate in methanol are then added. After 48 hours at ambient temperature, the volatile products are distilled under reduced pressure; the residue is solubilised in an equivalent weight of n-butanol and the solution is washed twice with boiling water. It is dried by heating under reduced pressure.

The product obtained is a brown oil which is soluble in water after neutralisation with lactic acid.

Base number: 1 meq/g.

EXAMPLE 8

Preparation of a mixture of compounds of the general formula (I) in which:
$R_1 = C_{10}H_{21}$
$R_2 = C_{14}H_{29}$
$p = 1$
$n = 5$
$G =$

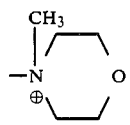

3.8 g (that is to say 0.03 mol) of dimethyl sulphate are added dropwise at ambient temperature, whilst stirring, to 30 g (that is to say 30 meq of amine) of compounds prepared in accordance with Example 7.

The temperature is left to rise to 45° C.

The mixture is kept at 45° C. for 2 hours after the addition has ended.

The product is a water-dispersible brown paste.

EXAMPLE 9

Preparation of a mixture of compounds of the general formula (I) in which:
$R_1 = C_{16}H_{33}$
$R_2 =$

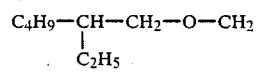

$p = 1$
$n = 6$
$G =$

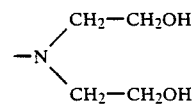

(a) Preparation of the compound of the general formula (II)

4.8 g of a solution of Na methylate in methanol (30 meq) are added to 500 g (2 mols) of molten hexadecan-1-ol.

The temperature is raised to 150° C., under nitrogen, and 186 g (1 mol) of 2-ethylhexyl glycidyl ether are added. The reaction mixture is kept at 150° C. for a further 4 hours after the addition has ended, and the excess alcohol is then distilled under reduced pressure.

The remaining product is neutralised with hydrochloric acid and then washed twice with its own weight of boiling water.

After drying by heating under reduced pressure, the most volatile constituents are separated off by molecular distillation at 130° C./1.33.10$^{-3}$ mbars.

The residue is subsequently distilled at 220° C./1.33.10$^{-3}$ mbars and the distillate is then rectified at 175° C./1.33.10$^{-2}$ mbars.

A colourless oil having a melting point of 9°-10° C. and a hydroxyl number of 2.27 meq/g is thus obtained.

(b) Preparation of the mixture of polychlorinated compounds of the general formula (IV)

0.38 ml of BF$_3$ etherate is added to 55.6 g (that is to say 0.13 mol) of the product thus prepared, and 72.1 g (that is to say 0.78 mol) of epichlorohydrin are then added dropwise at 55° C.

An oil having a hydroxyl number of:

$N_{OH} = 1.23$ meq/g is thus obtained.

(c) Preparation of a mixture of compounds of the general formula (VII)

17.3 g (0.165 mol) of diethanolamine and then 138 g of butyldiglycol are added to 121 g (that is to say 150 meq of —OH groups) of the product obtained, heated to 90° C. The temperature of the mixture is kept at 90° C. for 2 hours, 16.6 g of a 40% strength aqueous solution of NaOH are then added and the mixture is heated for a further 2 hours at 90° C. The product is washed twice with 270 ml of boiling water, and the organic phase is dried by heating under reduced pressure.

(d) Preparation of the mixture of compounds of the general formula (I)

62.6 g (that is to say 0.64 mol) of potassium acetate are added to 125 g (that is to say 593 meq of Cl) of the compounds obtained, solubilised in 125 g of butyldiglycol. The mixture is heated at 180° C. for 7 hours.

After the inorganic salts have been separated off, the organic phase is concentrated under reduced pressure at 180° C.

24.8 g of a 40% strength aqueous solution of NaOH are added to the product thus obtained and the mixture is heated at 90° C. for 1 hour.

The mixture is washed three times with 200 ml of boiling water, and the organic phase is then dried by heating under reduced pressure.

An oil is thus obtained, which is soluble in water after the addition of lactic acid.

Amine number: 1.03 meq/g.

EXAMPLE 10

Preparation of a mixture of compounds of the general formula (I) in which:
$R_1 = C_{16}H_{33}$
$R_2 =$

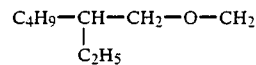

$p = 1$
$n = 6$
$G =$

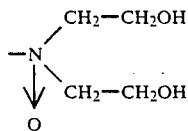

1.8 ml of hydrogen peroxide of 130 volumes strength (that is to say 0.021 mol) are added dropwise, at 45° C., to 20 g (that is to say 0.021 mol) of compounds obtained in accordance with Example 9.

The temperature is kept at 45° C. for 4 hours.

A water-dispersible, amber-coloured viscous oil is obtained.

EXAMPLE 11

Mixture of compounds of the general formula (I) in which:
$R_1 = C_{16}H_{33}$
$R_2 =$

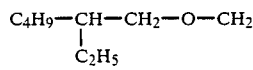

$p = 1$
$n = 6$
$G =$

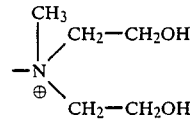

$CH_3SO_3^\ominus$ 2.3 g (0.021 mol) of methyl methanesulphonate are added dropwise, at ambient temperature, to 20 g (0.021 mol) of compounds obtained in accordance with Example 9.

The temperature rises to 37° C. and is maintained for 8 hours.

The product obtained is in the form of a water-soluble amber-coloured oil of high viscosity.

EXAMPLE 12

Preparation of a mixture of compounds of the formula (I) in which:
$R_1 = R_2 = C_{16}H_{33}$
$p = 1$
$n = 15$
$G =$

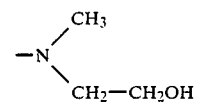

(a) Mixture of compounds of the general formula (II)

5.1 g (30 meq) of a solution of sodium methylate in methanol (containing 5.85 meq/g) are added to 435.6 g (1.8 mols) of molten hexadecanol marketed under the name Alfol 16 by CONDEA.

The methanol is distilled under reduced pressure, the residue is heated to 145° C. under a nitrogen atmosphere and 162 g (0.6 mol) of 1,2-epoxyoctadecane are then added dropwise.

The reaction mixture is kept at 145° C. for 3 hours and then washed three times with 500 ml of boiling water.

The organic phase is dried by heating under reduced pressure. The excess alcohol is distilled under reduced pressure and the volatile products are then removed by molecular distillation at 150° C./1.33.10$^{-3}$ mbars. The product is then distilled at 210° C./1.33.10$^{-3}$ mbars. A white wax having a melting point of 70° C. is obtained.

(b) Preparation of a mixture of polychlorinated compounds of the formula (IV)

0.33 ml of BF$_3$ etherate is added to 35.7 g (0.07 mol) of the compounds thus prepared, in the molten state, and 97 g (that is to say 1.05 mols) of epichlorohydrin are then added dropwise, whilst keeping the temperature at 55° C.

A further 0.20 ml of BF$_3$ etherate is added halfway through the addition and another 0.27 ml is then added after the addition has ended.

After 1 hour 30 minutes at 50° C., an oil having a hydroxyl number of 0.77 meq/g is obtained.

(c) Preparation of a mixture of compounds of the general formula (VII)

17.2 g, that is to say 0.23 mol, of N-methylethanolamine are added to 120 g of the product obtained above (that is to say 92.4 meq of OH groups), heated to 90° C.

The mixture is subsequently heated at 90° C. for 3 hours and then washed three times with 150 ml of boiling water. It is dried by heating under reduced pressure.

The product obtained has an amine number of 0.59 meq/g.

(d) Preparation of the mixture of compounds of the formula (I)

82 g (0.83 mol) of anhydrous potassium acetate are added to 110 g (795 meq of Cl) of the compounds thus obtained, solubilised in 110 g of dipropylene glycol. The mixture is then heated at 180° C. for 5 hours under a nitrogen atmosphere. The inorganic salts are filtered off and the dipropylene glycol is distilled under reduced pressure.

22 g of an aqueous solution of NaOH containing 10 meq/g are added to the residue thus obtained. The mixture is kept at 90° C. for 1 hour and then washed three times with 200 ml of boiling water. The dried product is a brown paste dissolving in water with a slight turbidity, which disappears on adding a small amount of lactic acid.

Base number: 0.61 meq/g.

EXAMPLE 13

Preparation of a mixture of compounds of the general formula (I) in which:
$R_1 = C_6H_{13}$
$R_2 = C_{12}H_{25}$
$p = 1$
$n = 4$
$G =$

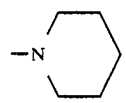

(a) Preparation of the compound of the formula (II)

1 g of sodium is added to 510 g of n-hexanol (5 mols).

After stirring for 2 hours at ambient temperature, the mixture is heated to 100° C. and 212 g of 1,2-epoxydodecane are then added in the course of 1 hour.

After heating for a further 2 hours at 100°-105° C., the excess alcohol is distilled, followed, at 156° C./1.33.10$^{-2}$ mbars, by a product which is in the form of a white solid at ambient temperature.

(b) Preparation of a mixture of polychlorinated compounds of the general formula (IV)

0.9 ml of BF$_3$/ether complex is added to 135 g (that is to say 0.43 mol) of the derivative thus obtained, in the molten state. The temperature is raised to 55° C. and 159 g (that is to say 1.72 mols) of epichlorohydrin are then added dropwise.

The mixture is kept at 55° C. for a further 30 minutes after the addition has ended.

The product thus obtained has a hydroxyl number of 1.59 meq/g.

(c) Preparation of a mixture of compounds of the general formula (VII)

14.9 g of piperidine, that is to say 0.175 mol, are added to 100 g (that is to say 159 meq of —OH) of the polychlorinated compounds obtained above. The mixture is kept at 90° C. for 2 hours and 17.6 g of an aqueous solution of NaOH containing 10 meq/g are then added. The mixture is heated for a further 2 hours.

The product is then washed twice with 150 ml of boiling water and dried by heating under reduced pressure.

(b) Preparation of the mixture of compounds of the general formula (I)

36.7 g of anhydrous potassium acetate (that is to say 374 meq) are added to 87 g of the product thus obtained (that is to say 350 meq of Cl), dissolved in 87 g of dipropylene glycol. The temperature is raised to 180° C. for 6 hours, under nitrogen. The precipitate is then filtered off, the dipropylene glycol is distilled and 19 g of an aqueous solution of NaOH containing 10 meq/g are added to the residue. The ingredients are left in contact for 1 hour at 90° C. and the mixture is then washed three times with 150 ml of boiling water.

The dried product is in the form of a brown oil which is soluble in water in the presence of lactic acid.

EXAMPLE 14

Preparation of a mixture of compounds of the general formula (I) in which:
R$_1$=C$_{10}$H$_{21}$
R$_2$=C$_{14}$H$_{29}$
p=2
n=4
G=

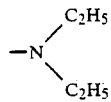

(a) Preparation of a mixture of intermediates of the general formula (II)

1.3 ml of BF$_3$ etherate are added to 79 g (0.5 mol) of decan-1-ol. The temperature is raised to 75° C. and 240 g (1 mol) of molten 1,2-epoxyhexadecane are then added dropwise. The temperature is kept at 75° C. for 1 hour after the addition has ended.

(b) Preparation of a mixture of polychlorinated compounds of the general formula (IV)

A further 0.72 ml of BF$_3$ etherate is added to the product thus prepared, and 181 g (1.96 mols) of epichlorohydrin are then added dropwise at 55° C. A brown oil having a hydroxyl number of 1.14 meq/g is obtained.

(c) Preparation of a mixture of compounds of the general formula (VII)

9.2 g of diethylamine (that is to say 125 meq) are added dropwise to 100 g of the above polychlorinated products (114 meq of hydroxyl groups), heated to 80° C. The mixture is kept at 80° C. for about 1 hour after the addition, and 12.6 g of a NaOH solution containing 10 meq/g, that is to say 126 meq, are then added.

The mixture is heated at 90° C. for a further 4 hours and then washed three times with 200 ml of boiling water and dried by heating under reduced pressure.

The product obtained has an amine number of 0.93 meq/g.

(d) Preparation of a mixture of compounds of the general formula (I)

25.7 g (that is to say 262 meq) of anhydrous potassium acetate are added to 83 g (that is to say 238 meq of organic Cl) of the compounds thus obtained, dissolved in 94 g of dipropylene glycol. The mixture is heated at 180° C. for 6 hours, under a nitrogen atmosphere.

The potassium chloride formed is filtered off and the dipropylene glycol is distilled under reduced pressure.

2.7 g of an aqueous solution of NaOH containing 10 meq/g are added to the residue thus obtained, and the mixture is heated at 90° C. for 1 hour.

The diluted product is then washed three times with 50 ml of isopropanol and 150 ml of boiling water. It is then dried by heating under reduced pressure.

The product obtained is an amber-coloured oil which is dispersible in water in the pressure of lactic acid.

The amine number is 0.90 meq/g.

EXAMPLE 15

Preparation of a mixture of compounds of the general formula (I) in which:
R$_1$=oleyl radical
R$_2$=mixture of C$_9$ to C$_{12}$ alkyl radicals
p=2
n=8
G=

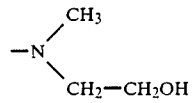

(a) Preparation of a mixture of compounds of the general formula (II)

0.65 ml of BF$_3$ etherate is added to 67 g (0.25 mol) of oleyl alcohol.

The temperature is raised to 50° C. and 96 g (500 meq of epoxide groups) of a mixture of α-epoxides containing C$_{11}$, C$_{12}$, C$_{13}$ and C$_{14}$ fatty chains are added dropwise.

The temperature is kept at 50° C. for 1 hour after the addition has ended.

(b) Preparation of a mixture of compounds of the general formula (IV)

A further 0.74 ml of BF$_3$ etherate is added and 185 g (2 mols) of epichlorohydrin are added, still at a temperature of 50° C. OH number: 0.86 meq/g.

(c) Preparation of a mixture of compounds of the general formula (VII)

11.1 g of methylethanolamine (148 meq) are added at 90° C., in the course of 15 minutes, to 150 g of the polychlorinated compounds prepared above. The mixture is heated at 90° C. for 3 hours. 14.9 g of 40% strength NaOH solution are then added and the mixture is heated at 90° C. for a further 2 hours 30 minutes.

The reaction mixture is washed three times with 200 ml of boiling water, in the presence of 50 to 100 ml of isopropanol. 130 g of compounds having a base number of 0.65 meq/g are thus obtained. 130 g of dipropylene glycol and 65.5 g of potassium acetate (668 meq) are added and the mixture is heated at 180° C. for 6 hours.

After the salts have been filtered off and the dipropylene glycol distilled, 15 g of 40% strength NaOH solution are added and the mixture is heated at 90° C. for 1 hour. It is then washed three times with 200 ml of boiling water, if appropriate in the presence of butanol in order to facilitate decantation.

After drying under reduced pressure, a very viscous brown oil is obtained, which gives a slight opalescence in water in the presence of lactic acid.

EXAMPLE 16

Preparation of a mixture of compounds of formula (I) in which:
$R_1 = C_4H_9$
$R_2 = $ oleyloxymethyl $C_{18}H_{35}OCH_2-$
$p = 2$
$n = 6$
$G =$

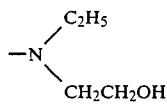

(a) Preparation of intermediate compounds of the formula (II)

To 3.7 g or 0.05 mole of n-butanol, is added 0.11 ml of $SnCl_4$. The temperature is raised to 55° C. and 33.7 g (0.1 mole) of oleylglycidylether (97%) is added, drop by drop, over 1 hour 20 minutes whilst maintaining this temperature.

(b) Preparation of a mixture of polychlorinated compounds of the general formula (IV)

To 34.4 g of the preceding derivative are added 0.08 ml of $SnCl_4$ and at this same temperature 26.4 g (0.285 mole) of epichlorohydrin, drop by drop, over 1 hour 30 minutes.

OH Index: 0.90 meq/g (c) Preparation of a mixture of compounds of the general formula (VII)

4.3 g (47.5 meq) of N-ethylaminoethanol (98%) are added, at 90° C., over 20 minutes, to 48 g of the polychlorinated compounds previously prepared and after leaving the mixture for 1 hour at the temperature, 4.9 g (47.5 meq) of 40% NaOH solution is added over 15 minutes and then heated to 90° C. for a further 2 hours.

The reaction mixture is washed twice with 120 ml of boiling water and then dried in vacuo and the resulting product filtered on sintered glass No. 4 to obtain a clear yellow product having an amine index of 0.75 meq/g.

To 49.5 g of this product is added 50 g of dipropyleneglycol and 20.4 g of potassium acetate (208 meq) and the mixture heated to 180° C. for four hours under a nitrogen atmosphere.

After filtering the salts and distillation of the dipropyleneglycol, the product is solubilised in 50 g of n-butanol and 5.2 g of 40% NaOH solution added and the mixture heated to 90° C. for 1 hour and then washed twice with 100 ml of boiling water.

After drying under reduced pressure 41 g of a viscous brown oil is obtained which is dispersible in water soluble after neutralisation with an excess of lactic acid.

Amine Index: 0.52 meq/g.

APPLICATION EXAMPLES

EXAMPLE A1

| Microemulsion | |
|---|---|
| Vaseline oil (liquid petrolatum) | 30 g |
| Cetyl laurate sold under the trademark "Cetiol LC" by Henkel | 10 g |
| Compounds prepared in accordance with Example 7 | 9 g |
| Compounds prepared in accordance with Example 4 | 1 g |
| Preservative | 0.1 g |
| Perfume | 0.2 g |
| Water q.s.p. (quantity sufficient for) | 100 g |

EXAMPLE A2

| Rinsed lotion (rinse) | |
|---|---|
| Compounds according to Example 12 | 0.7 g |
| Cetyl/stearyl alcohol sold under the trademark "lanette wax" by Henkel | 2 g |
| Mixture of fatty alcohols and oxyethyleneated products, sold under the trademark "POLAWAX GP 200" by Croda Ltd. | 2 g |
| Hydroxyethylcellulose sold under the trademark "Cellosize QP 4400" by Union Carbide | 0.8 g |
| Quaternary dialkylammonium chloride sold under the trademark "ARQUAD 2 HT" by Akzo | 2.5 g |
| Alkyl-dimethylhydroxyethyl-ammonium chloride containing 30% of AI (active ingredient) | 2 g |
| Water q.s.p. | 100 g |

The pH is adjusted to 6.5 with HCl.

EXAMPLE A3

| Rinsed lotion (rinse) | |
|---|---|
| Compounds according to Example 3 | 1 g |
| Cetyl alcohol | 6 g |
| Cetyl/stearyl alcohol oxyethyleneated with 15 mols of ethylene oxide, sold under the trademark "Cemulsol OR 30" by S.P.C.S. | 3 g |
| Mixture of fatty alcohols and oxyethyleneated products, sold under the trademark "Polawax EP 100" by Croda | 2 g |
| Alkyl-trimethylammonium chloride | 1.5 g |
| Hydroxyethylcellulose sold under the trademark "Natrosol 250 HHR" by Hercules | 0.4 g |
| Water q.s.p. | 100 g |

The ph is adjusted to 5.8 with NaOH.

EXAMPLE A4

| Shampoo | |
|---|---|
| Compounds according to Example 9 | 2.5 g |
| Sorbitan monolaurate polyoxyethyleneated with 20 mols of ethylene oxide, sold under the trademark "TWEEN 20" by Atlas Non-ionic surface-active agent of the formula: | 6.2 g |

-continued

| Shampoo | |
|---|---|
| $C_{12}H_{25}(OCH_2-CH)_n OH$, in which n denotes an $\phantom{xxxxxxxxxxxxxxx}\vert$ $\phantom{xxxxxxxxxxxxxx}CH_2OH$ average statistical value of 4.2, containing 60% of AI | 12 g |
| Mixed sodium and triethanolamine salts of lipoaminoacids obtained by combining lauric acid with the aminoacids produced by the total hydrolysis of collagen, containing 22% of active ingredient, sold under the trademark "LIPOPROTEOL LTO" by Rhone Poulenc | 4 g |
| Water q.s.p. | 100 g |

The pH is adjusted to 7.4 with HCl.

EXAMPLE A5

| Shampoo | |
|---|---|
| Compounds according to Example 8 | 0.7 g |
| Lauryl alcohol oxyethyleneated with 12 mols of ethylene oxide | 3 g |
| Non-ionic surface-active agent of the formula: $RCHOH-CH_2O-(CH_2CHOH-CH_2O)_n H$ R: $C_9-C_{12}$ alkyl n: average statistical value of 3.5 | 10 g |
| Nonylphenol oxyethyleneated with 9 mols of ethylene oxide, sold under the trademark "ANTAROX CO 630" by G.A.F. | 5 g |
| Lauryl diethanolamide | 2 g |
| Water q.s.p. | 100 g |

The pH is adjusted to 6.7 with NaOH.

EXAMPLE A6

| Shampoo | |
|---|---|
| Compounds according to Example 7 | 1.8 g |
| Na salt of sulphated $C_{12}-C_{14}$ alkanol oxyethyleneated with 2.2 mols of ethylene oxide, aqueous solution containing 25% of active ingredient | 25 g |
| Surface-active agent of the formula: $R-(OCH_2CH_2)_{10}OCH_2COOH$ R: mixture of $C_{12}-C_{14}$ alkyl radicals (aqueous solution containing 90% of active ingredient), sold under the trademark "AKYPO RLM 100" by CHEM'Y | 10 g |
| Copra diethanolamides | 2.5 g |
| NaCl | 1.5 g |
| Water q.s.p. | 100 g |

The pH is adjusted to 6.9 with NaOH.

EXAMPLE A7

| Shampoo | |
|---|---|
| Compounds according to Example 6 | 0.1 g |
| Sodium salt of sulphated oxyethyleneated lauryl alcohol, containing 30% of active ingredient | 12 g |
| Surface-active agent of the formula: $R(OCH_2CH_2)_{10}OCH_2COOH$ R: mixture of $C_{12}-C_{14}$ alkyl radicals (in the form of an aqueous solution containing 90% of active ingredient), sold under the trademark "AKYPO RLM 100" by CHEM'Y | 8 g |
| Mixture of olefine-sulphonates of the formulae: $CH_3(CH_2)_{10-12}CH=CH-CH_2-SO_3Na$ and | 5 g |
| $CH_3(CH_2)_{10-12}CH-CH_2-CH_2-SO_3Na$ $\phantom{xxxxxxxxxxxxx}\vert$ $\phantom{xxxxxxxxxxxxx}OH$ containing 38% of active ingredient, sold under the trademark "ELFAN OS 46" by Akzo | |
| Copra diethanolamides | 1 g |
| NaCl | 2 g |
| Water q.s.p. | 100 g |

The pH is adjusted to 7.8 with HCl.

The compositions of Examples A2 to A7 make the hair easier to comb out when damp and give the hair shine, suppleness and lightness, without a weighing-down effect, when dry.

EXAMPLE A8

| MOISTURISING MILK | |
|---|---|
| Compounds according to Example 15 | 8 g |
| Vaseline oil (liquid petrolatum) | 20 g |
| Isopropyl palmitate | 10 g |
| Gelled lanoline sold under the trademark "Lantrol Gel" by N.L. Industry Corp | 5 g |
| Magnesium sulphate | 0.5 g |
| Propylene glycol | 3 g |
| Butylhydroxyanisole | 0.025 g |
| Butylhydroxytoluene | 0.025 g |
| Perfume | 0.2 g |
| Preservative | 0.2 g |
| Sterile demineralised water q.s.p. | 100 g |

This milk is in the form of an oil-in-water emulsion which spreads easily over the skin and makes it soft.

EXAMPLE A9

| BATH OIL | |
|---|---|
| Compounds according to Example 15 | 20 g |
| Cetyl laurate sold under the trademark "Cetiol LC" by Henkel | 70 g |
| Dimethyllauramine oleate sold under the trademark "Necon LO" by Nicon | 2.5 g |
| Butylhydroxyanisole | 0.05 g |
| Butylhydroxytoluene | 0.05 g |
| Perfume | 0.1 g |

EXAMPLE A10

| BODY FLUID | |
|---|---|
| Compounds according to Example 15 | 10 g |
| Cationic polymer consisting of repeat units of the formula: | 1 g |

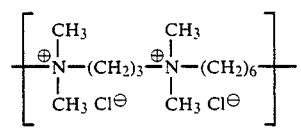

| | |
|---|---|
| Isopropyl myristate | 20 g |
| Vaseline oil | 20 g |
| Butylhydroxyanisole | 0.03 g |
| Butylhydroxytoluene | 0.03 g |
| Perfume | 0.15 g |
| Preservative | 0.1 g |
| Sterile demineralised water q.s.p. | 100 g |

This is a fluid oil-in-water emulsion which spreads easily over the skin and makes it soft to the touch.

EXAMPLE A11

| MAKE-UP REMOVAL GEL FOR THE SKIN | |
|---|---|
| Compounds according to Example 15 | 12 g |
| Butylhydroxyanisole/butylhydroxytoluene (1/1) | 0.04 g |
| Glycerol | 3 g |
| Perfume | 0.15 g |
| Preservative | 0.1 g |
| Sterile demineralised water q.s.p. | 100 g |

In example A2 compounds according to Example 11 may replace compounds according to Example 12.

In Example A3 compounds according to Example 13 or 14 may replace compounds according to Example 3.

In Example A4 compounds according to Example 2 may replace compounds according to Example 9.

In Example A5 compounds according to Example 5 or 10 may replace compounds according to Example 8.

In Example A7 compounds according to Example 1 may replace compounds according to Example 6.

We claim:

1. A composition that is suitable for use in cosmetics comprising a diluent or a suitable cosmetic vehicle and at least one cationic surface active product selected from the group consisting of cationic surface-active product having the general formula:

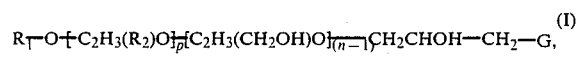

wherein $R_1$ denotes a linear or branched, saturated or unsaturated aliphatic radical containing from 4 to 20 carbon atoms; $R_2$ is selected from the group consisting of a linear or branched alkyl radical having from 4 to 20 carbon atoms, a linear or branched alkoxymthyl radical in which the alkoxy portion has from 4 to 20 carbon atoms, and a linear alkenyloxy radical in which the alkenyl portion has from 4 to 20 carbon atoms; p denotes an integral or decimal number from 1 to 2.5; n denotes an integral or decimal number from 2 to 20, and G is a substituent group selected from the group of substituents consisting of the following:

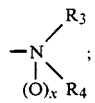 (a)

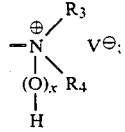 (b)

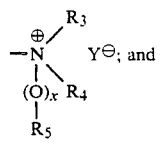 (c)

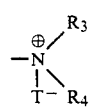 (d)

in which x denotes 0 or 1; $R_3$ and $R_4$ independently denote an alkyl or hydroxyalkyl radical having from 1 to 3 carbon atoms or, alternatively, $R_3$ and $R_4$ together with the nitrogen atom to which they are attached form a 5- or 6- membered heterocyclic ring; V denotes an anion of a mineral or organic acid; $R_5$ denotes an alkyl or hydroxyalkyl radical having from 1 to 3 carbon atoms; Y denotes an anion; and T denotes a methylcarboxylate or propylsulphonate anion.

2. The composition of claim 1, wherein $R_1$ denotes a linear or branched saturated aliphatic radical containing from 6 to 18 carbon atoms and $R_2$ is selected from the group consisting of linear or branched alkyl radicals having from 8 to 20 carbon atoms.

3. A composition according to claim 1, which contains at least 0.05% by weight of product of formula (I), relative to the total weight of the composition.

4. A composition according to claim 3, which contains from 0.2 to 20% by weight of product of formula (I).

5. A composition according to claim 1 wherein said composition is selected from the group consisting of an aqueous of aqueous-alcoholic solution or dispersion, an emulsion, a powder, a wax, a microemulsion, a gel, an oil, an oily-alcoholic composition and an aerosol.

6. A composition according to claim 5 which also contains at least one non-ionic, anionic, cationic or amphoteric surface-active agent, animal, mineral, vegetable or synthetic oil or wax, anionic, cationic, non-ionic or amphoteric cosmetic resin, thickener, opacifier, preservative, perfume, dyestuff, alcohol having 1 to 6 carbon atoms, pH modifier, natural substance or other substance active in the treatment, care or protection of the skin or hair.

7. An oil-in-water emulsion which contains at least one product as defined in claim 1.

8. A process for treating the hair or skin which comprises applying thereto a composition as defined in claim 1.

* * * * *